(12) United States Patent
Sansone (10) Patent No.: US 6,754,366 B2
(45) Date of Patent: *Jun. 22, 2004

(54) METHOD FOR DETERMINING IF MAIL CONTAINS LIFE HARMING MATERIALS

(75) Inventor: Ronald P. Sansone, Weston, CT (US)

(73) Assignee: Pitney Bowes Inc., Stamford, CT (US)

( * ) Notice: Subject to any disclaimer, the term of this patent is extended or adjusted under 35 U.S.C. 154(b) by 564 days.

This patent is subject to a terminal disclaimer.

(21) Appl. No.: 09/818,195

(22) Filed: Mar. 27, 2001

(65) Prior Publication Data

US 2002/0141613 A1 Oct. 3, 2002

(51) Int. Cl.[7] ............................................. G06K 9/00
(52) U.S. Cl. ....................... 382/101; 382/143; 382/102; 705/402; 705/406; 705/410; 209/584; 209/900
(58) Field of Search ............................... 382/101, 102, 382/139, 140, 143; 705/60, 401–411; 209/584, 900; 463/43

(56) References Cited

U.S. PATENT DOCUMENTS

| | | | |
|---|---|---|---|
| 4,037,956 A | | 7/1977 | McKeen, Jr. |
| 4,962,532 A | | 10/1990 | Kasiraj et al. |
| 5,079,714 A | * | 1/1992 | Manduley et al. ........... 700/219 |
| 5,086,300 A | * | 2/1992 | Ashmore ...................... 342/20 |
| 5,612,889 A | | 3/1997 | Pintsov et al. ......... 364/478.14 |
| 5,648,916 A | | 7/1997 | Manduley ............... 364/514 A |
| 5,838,768 A | | 11/1998 | Sumar et al. .................. 379/89 |
| 5,974,449 A | | 10/1999 | Chang et al. |
| 6,047,272 A | | 4/2000 | Biliris et al. |
| 6,064,995 A | * | 5/2000 | Sansone et al. ............. 705/410 |
| 6,072,862 A | | 6/2000 | Srinivasan ............. 379/100.08 |
| 6,273,267 B1 | | 8/2001 | Tamamoto et al. |
| 6,285,777 B2 | | 9/2001 | Kanevsky et al. |
| 6,289,323 B1 | | 9/2001 | Gordon et al. |
| 6,293,037 B1 | | 9/2001 | Spada et al. |
| 6,390,921 B1 | | 5/2002 | Busch et al. |
| 6,542,584 B1 | | 4/2003 | Sherwood et al. |
| 2002/0002590 A1 | | 1/2002 | King et al. |
| 2002/0042808 A1 | | 4/2002 | Smith et al. |
| 2002/0095306 A1 | | 7/2002 | Smith et al. |
| 2002/0165729 A1 | | 11/2002 | Kuebert et al. |

FOREIGN PATENT DOCUMENTS

| | | | |
|---|---|---|---|
| DE | 197 45 641 A1 | 11/1999 | |
| EP | 0 375 139 A2 | 11/1989 | |
| EP | 0 465 011 A2 | 1/1992 | |
| EP | 1063602 A1 | 12/2000 | |
| WO | WO 99/21330 | 10/1998 | ........... H04L/12/58 |
| WO | WO 02/01434 A1 | 1/2002 | |
| WO | WO 02/42979 A1 | 5/2002 | |

OTHER PUBLICATIONS

Pitney Bowes Inc. Software Solutions regarding ReUnion™ *Data Quality to a New Level* dated 1998.
Pitney Bowes Inc. Software Solutions regarding FinalFocus™ *Your Single Source for Geographic. Demographic and Lifestyle Information* dated 1998.

* cited by examiner

Primary Examiner—Amelia M. Au
Assistant Examiner—Charles Kim
(74) Attorney, Agent, or Firm—Ronald Reichman; Angelo N. Chaclas (57) ABSTRACT

A method that enables the carrier of letters, flats and/or packages (mail) that are addressed to a recipient to determine if the mail contains life harming materials, before the mail is delivered to the recipient. The invention accomplishes the foregoing by receiving mail that is addressed to a recipient which contains material that may or may not be life harming; capturing an image of the face of the mail, which includes the name and physical address of the recipient; processing the image on the face of the mail to determine if characteristics of the image match characteristics of known mail that may contain life harming materials; testing the mail if the image contains characteristics of life harming material; and delivering the mail to the recipient if the image does not contain life harming characteristics.

8 Claims, 11 Drawing Sheets

METHOD FOR DETERMINING IF MAIL CONTAINS LIFE HARMING MATERIALS

CROSS REFERENCE TO RELATED APPLICATIONS

Reference is made to commonly assigned copending patent applications Ser. No. 09/818,792 filed Mar. 27, 2001, entitled "Recipient Elected Messaging Services" in the names of Ronald P. Sansone, Robert A. Cordery and Donald G. Mackay; Ser. No. 09/818,721 filed Mar. 27, 2001, entitled "Sender Elected Messaging Services" in the names of Ronald P. Sansone, Robert A. Cordery and Donald G. Mackay; Ser. No. 09/817,998 filed Mar. 27, 2001, entitled "Messaging Services for Visually Impaired" in the name of Ronald P. Sansone; Ser. No. 09/818,800 filed Mar. 27, 2001, entitled "Messaging Services For Uniquely Identified Mail" in the name of Ronald P. Sansone; Ser. No. 09/818,480 filed Mar. 27, 2001, entitled "Recipient Elected Messaging Services For Mail That Is Transported In Trays Or Tubs" in the name of Ronald P. Sansone; Ser. No. 09/818,727 filed Mar. 27, 2001, entitled "A Method For A Carrier to Determine The Location Of A Missing Person" in the name of Ronald P. Sansone; and Ser. No. 10/138,967, filed Nov. 7, 2003, entitled "Recipient Elected Messaging Services Enabled By Processing Codes Printed On Mail".

FIELD OF THE INVENTION

The invention relates generally to the field of mail delivery systems and, more particularly, to methods that detect the presence of life harming materials.

BACKGROUND OF THE INVENTION

People have directly transmitted information from one person to another. Information was first transmitted by spoken word and later by written word. Writings enabled people to transmit information by messengers from a location in which the sender of the writing was present to another location where the receiver was present. In time, postal services were developed in which a person would deliver letters to the post office in one city, and an agent of the post office would deliver that letter to a post office in another city, where the letter mail would be picked up by the person to whom the letter was sent.

Ever since the numeric codification of streets and buildings received general acceptance, an individual's name and household postal address have been linked. The sender of a letter or package would deliver a letter or package to the post that had the correct recipient postal address, and the post would deliver the letter or package to the numeric street address of the recipient of the letter or package. A correct recipient postal address for the delivery of the letter or package to the recipient included the name of the recipient; the street address of the recipient; the city and state of the recipient; and the zip code of the recipient. Thus, the correct recipient postal address is usually the actual location of the recipient.

People have used the post and other courier services, e.g., Federal Express®, Airborne®, United Parcel Service®, DHL®, etc., hereinafter called "carriers", to deliver materials to recipients that the sender does not want to deliver personally. Unfortunately, sometimes the delivered materials may be illegal and/or hazardous to the health of the recipient and to the party who is delivering the goods, e.g. life harming. Examples of life harming materials are explosives, gun powder, blasting material, bombs, detonators, smokeless powder, radioactive materials, ammunition, atomic weapons, chemical compounds or any mechanical mixture containing any oxidizing and combustible units, or other ingredients in such proportions, quantities, or packing that ignite by fire, friction, concussion, percussion or detonation of any part thereof which may and is intended to cause an explosion; poisons; carcinogenic materials; caustic chemicals; hallucinogenic substances; illegal materials; drugs that are illegal to sell and/or dispense; and substances which, because of their toxicity, magnification or concentration within biological chains, present a threat to biological life when exposed to the environment, etc.

SUMMARY OF THE INVENTION

This invention overcomes the disadvantages of the prior art by providing a method that enables the carrier of letters, flats and/or packages (hereinafter "mail") that are addressed to a recipient to determine if the mail contains life harming materials before the mail is delivered to the recipient. Thus, the carrier may be able to remove mail from the mail stream before it causes human harm and/or damages property.

This invention accomplishes the foregoing by receiving mail that is addressed to a recipient which contains material that may or may not be life harming; capturing an image of the face of the mail, which includes the name and physical address of the recipient; processing the image on the face of the mail to determine if characteristics of the image match characteristics of known mail that may contain life harming materials; testing the mail if the image contains characteristics that indicate a probability that the mail contains life harming material; and, delivering the mail to the recipient if the image does not contain life harming characteristics.

DETAILED DESCRIPTION OF THE PREFERRED EMBODIMENT

Figure 1A:
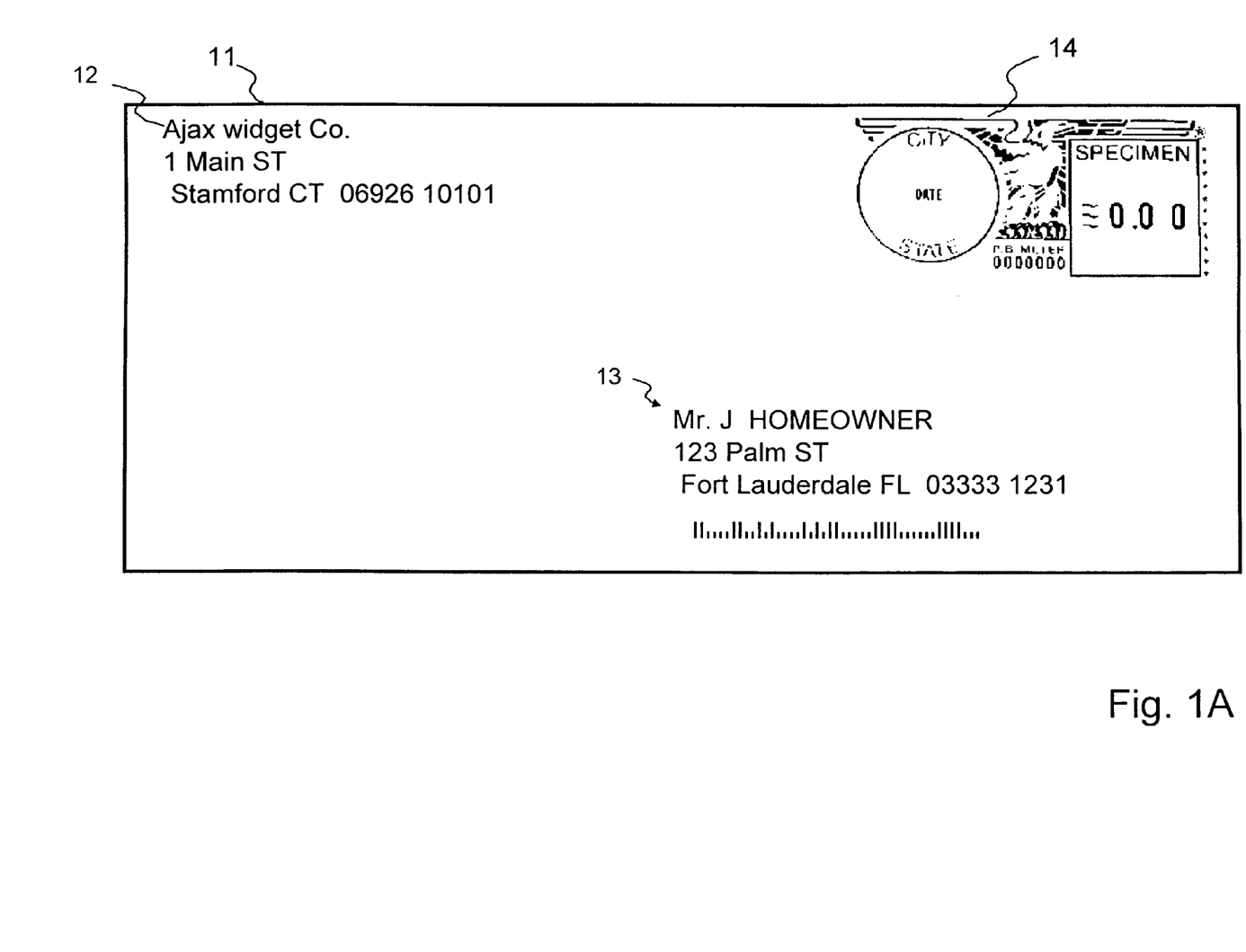
FIG. 1A is a drawing of a metered mailpiece.

Referring now to the drawings in detail and more particularly to FIG. 1A, the reference character 11 represents a mailpiece that has a sender address field 12, a recipient address field 13, and a postal indicia 14.

Figure 1B:
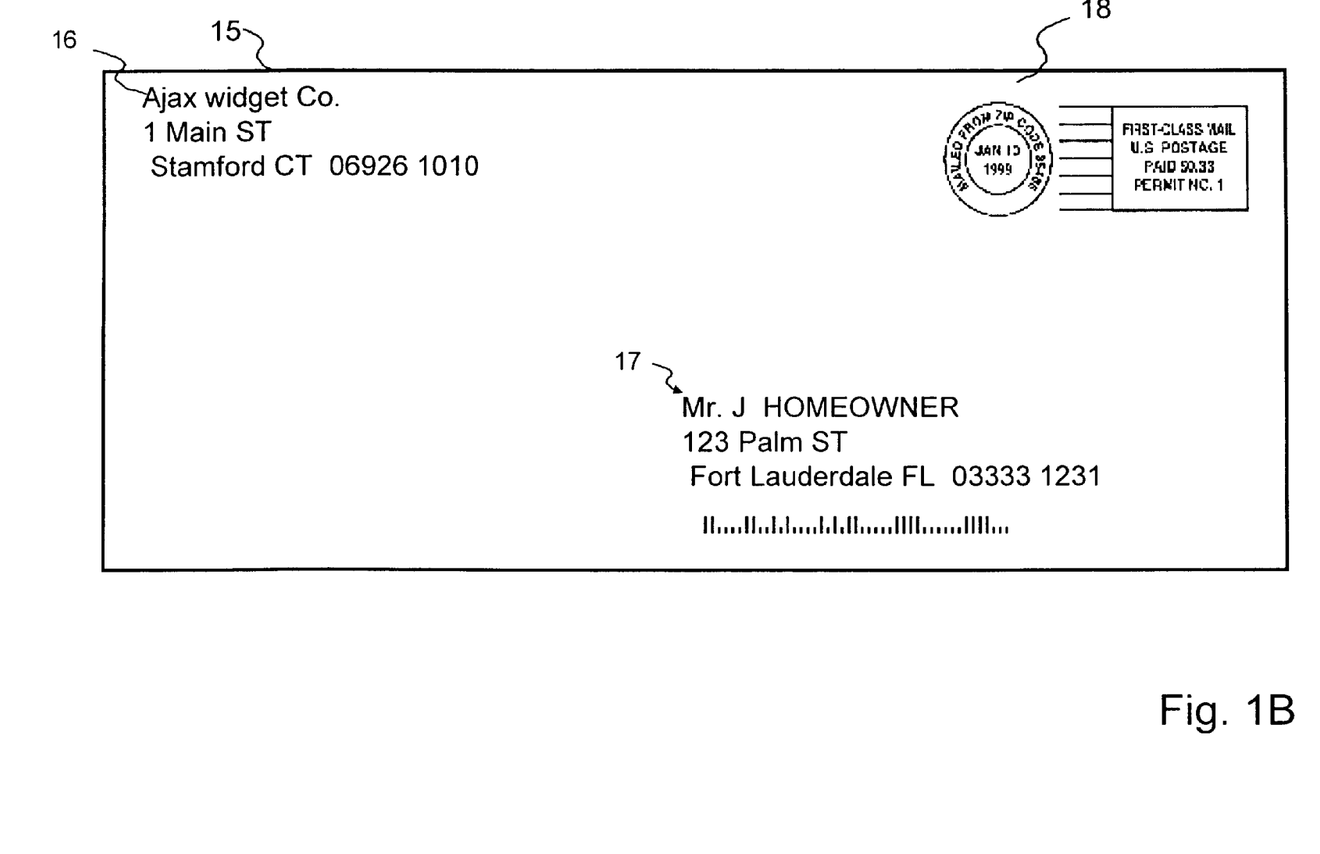
FIG. 1B is a drawing of a permit mailpiece.

FIG. 1B is a drawing of a permit mailpiece. Mailpiece 15 has a sender address field 16, a recipient address field 17, and a permit 18.

Figure 1C:
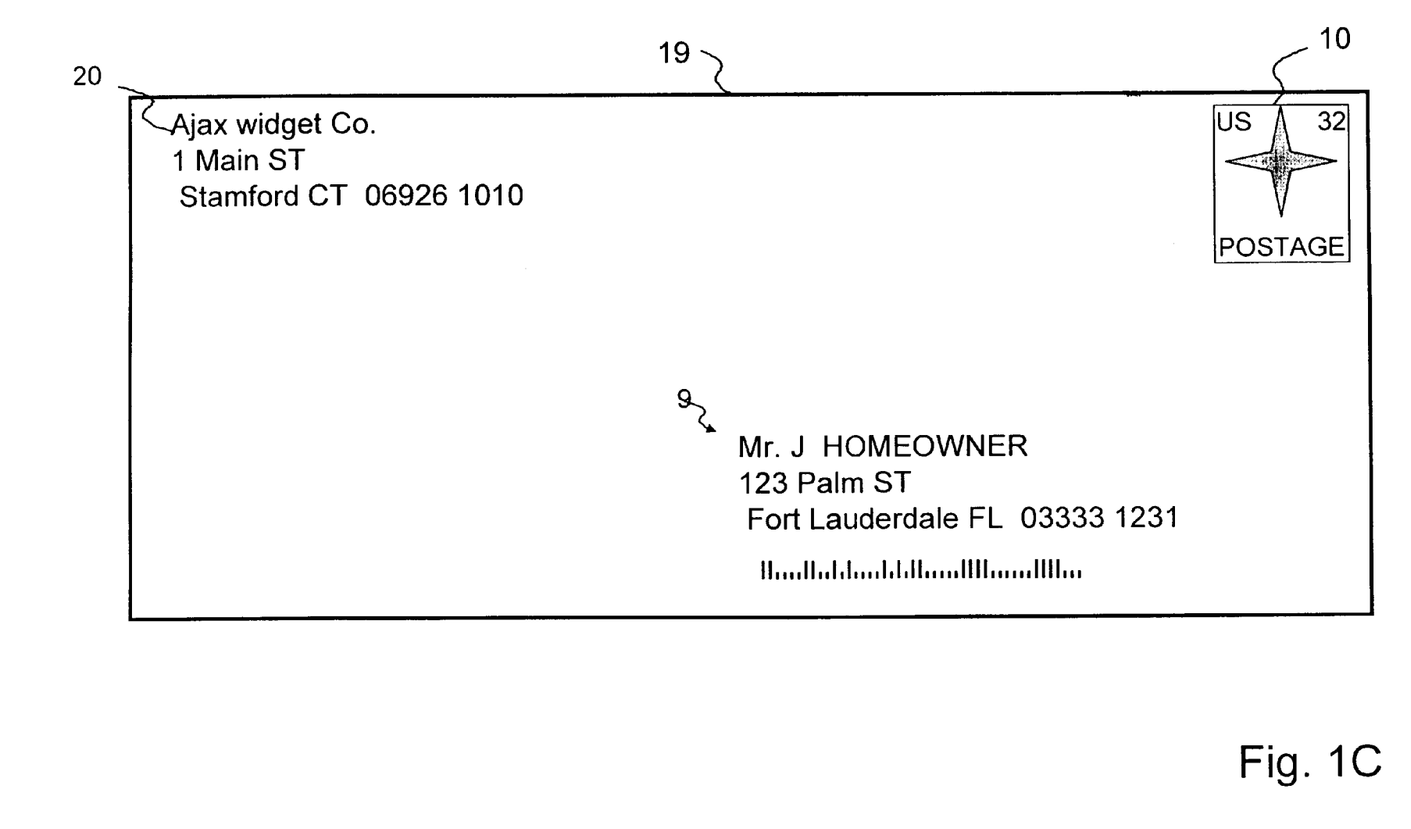
FIG. 1C is a drawing of a stamped mailpiece.

FIG. 1C is a drawing of a stamped mailpiece. Mailpiece 19 has a sender address field 20, a recipient address field 9, and a stamp 10.

Figure 1D:
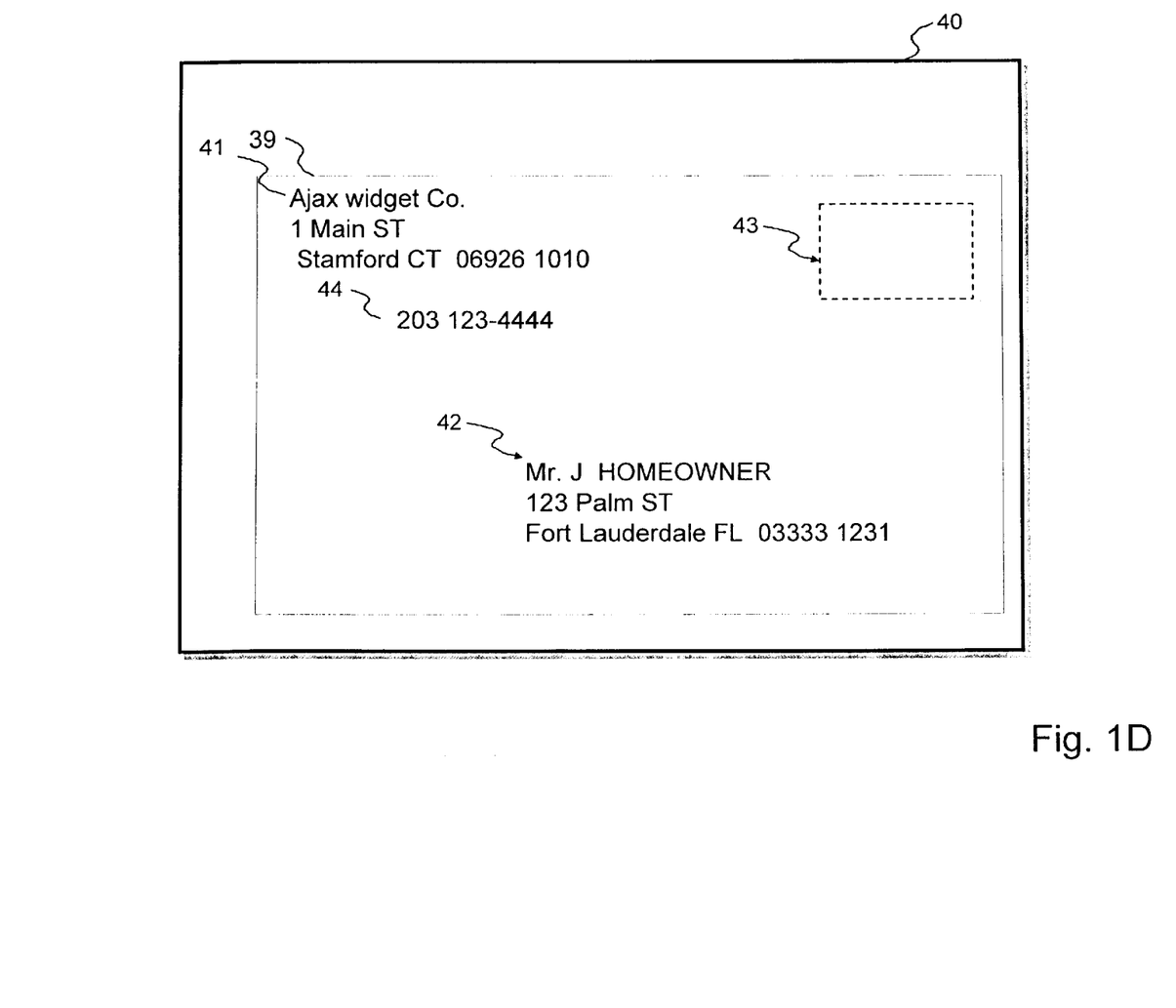
FIG. 1D is a drawing of a flat or package that is going to be delivered by a carrier.

FIG. 1D is a drawing of a flat or package that is going to be delivered by a carrier. Package 40 has a label 39 affixed thereto. Label 39 has a sender address field 41, a recipient address field 42, and may have other sender information, e.g., the sender's phone number 44. Indicia 43 is affixed to label 39. Indicia 43 may be a postal indicia or courier symbology.

Figure 2:
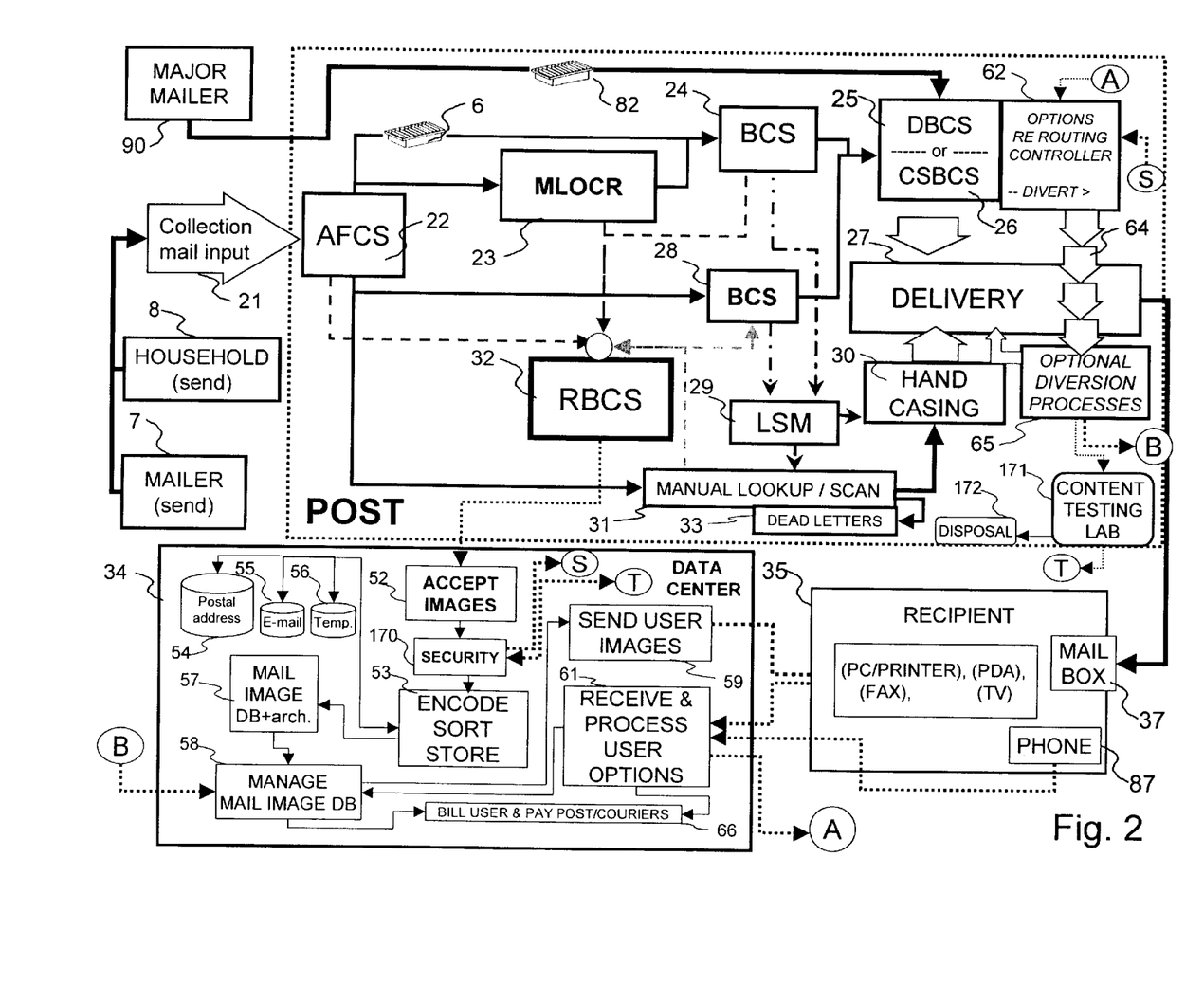
FIG. 2 is a drawing showing how this invention may be used by a post in the processing of letter mail.

FIG. 2 is a drawing showing how this invention may be used by a post in the processing of letter mail. Letter mail that is deposited in trays 6 and delivered to the post is read by multiple optical character reader (hereinafter "MLOCR") 23. Collection letter mail may be metered letter mail that is produced at a mailer site 7 or a sender household 8 by a postage meter or a personal computer meter; stamped mail; or permit mail. Collection letter mail is placed in collection mail input 21, e.g., mail boxes or delivered to the United States Postal Service unsorted. Collection letter mail is sent to advanced AFCS (hereinafter "AFCS") 22. AFCS 22 first faces the letter mail. Then AFCS 22 electronically identifies and separates prebarcoded mail, handwritten addresses and machine-imprinted address pieces for faster processing through automation. Letter mail that AFCS 22 determines is optical character readable is sent to multi-line optical character reader/code printer (hereinafter "MLOCR") 23. MLOCR 23 reads the entire address on the letter mail; sprays a bar code on the mail; and then sorts the mail. Letter mail that is able to be scanned and sorted by MLOCR 23 is sent to bar code sorter/code printer 24. Letter mail that the mailer has prebarcoded and contains a facing identification mark is sent to bar code sorter/code printer 24.

Trayed mail 82 (mail in which the sender is entitled to discounts) that is produced at a major mailer site 90 (FIG. 5) is sent to a delivery bar code sorter/code printer 25 or a carrier sequence bar code sorter/code printer 26. Sorters 25 and 26 sort the letter mail in the order that the mail is going to be delivered by postal carrier 27. Letter mail that AFCS 22 determines is not optical character readable is sent to bar code sorter/code printer 28. Letter mail that AFCS 22 obtains electronic images from and letter mail that MLOCR 23 obtains electronic images from transfers the electronic images to remote bar code system ("RBCS") 32. RBCS 32 matches the look up zip code for the letter mailpieces from AFCS 22 and merges them. RBCS 32 electronically transmits the bar code information to sorter 28 where the bar code information is sprayed on the mailpieces. Letter mail that is able to be scanned and sorted by sorters 24 and 28 is sent to a delivery bar code sorter 25. Sorters 25 and 26 sort the letter mail in the order that the mail is going to be delivered by postal carrier 27, or hold the mail for recipient diversion for a specified period of time in divert mail options rerouting controller 62.

Letter mail that can not be scanned and sorted by sorters 24 and 28 is sent to letter sort machine 29. Letter mail that can be sorted by letter sort machine (hereinafter "LSM") 29 is sent to postal hand casing 30. Postal hand casing 30 is the process in which the postal carrier sorts the letter mail in the order that the letter mail is going to be delivered by postal carrier 27. Letter mail that can not be sorted by LSM 29 is sent to manual lookup, scan and sortation process (hereinafter "manual process") 31. Manual process 31 attempts to classify the previously rejected letter mailpiece to redirect the mailpiece; declare the mailpiece dead; or, manually re-code the mailpiece for redelivery. Then the letter mailpieces that have not been processed in manual process 31 are sent to dead letters 33. In manual process 31, an operator may determine the address of the recipient and produce a label to be placed on the letter mail. Then the letter mail would go to postal hold casing 30 where the mail is sorted in the order that the mail is going to be delivered by postal carrier 27.

Letter mail that can not be faced and cancelled by AFCS 22 is sent to manual process 31. Manual process 31 attempts to classify the previously rejected letter mailpiece to redirect the mailpiece; declare the mailpiece dead; or manually re-code the mailpiece for redelivery. Then the letter mail that manual process 31 is able to classify is sent to postal carrier casing 30 before it is delivered by postal carrier 27.

RBCS 32 electronically transmits the bar code information that represents the destination of the letter mailpiece, the party to whom the mailpiece is to be delivered and the image of the face of the mailpiece to data center 34. The aforementioned scanners scan all of the information appearing on the face of the letter mail, e.g., (from FIG. 1A), the sender's name and address 12, the recipient's name and address 13, and postal indicia 14. The scanned information is transferred to accept process images 52. Now the scanned information is transferred to security process 170. Process 170 transfers information to options controller 62. Process 170 will be hereinafter described in the description of FIG. 6. If process 170 decides that there is no indication that the mailpiece does not contain life harming material, then the information is sent to encode, sort, store 53. At this point, the recipient's physical address is verified by checking postal address data base 54, and the recipient's e-mail address is determined from e-mail data base 55. Temporary data base 56 is then searched to determine whether or not the recipient has left any forwarding addresses. Encode 53 then encodes and sorts the information obtained from data bases 54, 55 and 56.

The aforementioned encoded and sorted information is stored in mail image data base 57. Then the mail image information is sent to manage mail image DB 58 where the various options and the costs associated therewith that the recipient may have for delivering the information contained in the letter mail are determined. Then the mail images and options that the recipient has for receiving the letter mail are sent to images 59, where the information appearing on the face of the letter mail in alphanumeric and graphic form and the options in alphanumeric and graphic form that the recipient has for receiving the letter mail are transmitted to receiving device 36 (personal computer, television, facsimile machine, personal data assistant, etc.), which is located at the recipient's business or household 35. The options that the recipient has for diverting the letter mail is described in the description of FIG. 4.

The recipient may use device 36 (personal computer, facsimile machine, personal data assistant, etc.) located at the recipient's business or household 35 to inform receive and process recipient options 61, located at data center 34, of the manner in which the letter mail should be delivered. The recipient may also use a touch tone and/or voice telephone 87 to inform options 61 of the manner in which the recipient would like the letter mail displayed on the receiving device 36, e.g., television delivered. For instance, the recipient may want the letter mail physically delivered to the recipient's house faster or slower, or the letter mail physically redirected to the recipient's temporary address, or physically delivered to the recipient's agent, or physically delivered to the recipient's attorney, or physically returned to the mailer, or have the post open the letter mail and have the post e-mail or fax the contents of the letter mail to the recipient and/or parties designated by the recipient.

At this juncture, the recipient may inform options 61 via a device 36 of the manner in which the recipient would like the letter mail processed. Options 61 will then inform the recipient via device 36 of the cost to the recipient to process the letter mail in the manner selected by the recipient. The recipient may then inform the post to deliver the letter mail in the manner selected by the recipient. The recipient's selected manner of letter mail processing is forwarded to options rerouting controller 62. If the post's specified time to deliver the letter mail has not been reached, the letter mail is sent to recipient options 64 and delivered in the manner selected by the recipient in route mail options 65. Then options 65 informs manage mail data base 58 to archive the image and also to notify bill sender and pay carriers 66 to bill the recipient and pay the post. At this point, the next letter mail image is ready to be processed.

The letter mail may then be delivered to the recipient at mail box 37 at a faster or slower rate than that selected by the sender; held by the post for a specified amount of time and then delivered to an address specified by the recipient; opened, and the contents of the letter mail faxed to recipient's selected fax numbers; opened, and the contents of the letter mail faxed to recipient's selected fax numbers and then the letter mail may be delivered to the physical address specified by the recipient; opened, and the contents of the letter mail e-mailed to recipient's selected e-mail addresses; or, opened, and the contents of the letter mail e-mailed to recipient's selected e-mail addresses, and then the letter mail may be delivered to the physical address specified by the recipient. The recipient may also have instructed the post to return the mail to the sender, to destroy the mail, or to recycle the paper in the letter mail. Options 61 will also send the cost of the recipient's selected manner of delivery to bill recipient 66 so that data center 34 may inform the post to debit the recipient's account or send a bill to the recipient.

If security process 170 determines there is an indication that the mailpiece contains life harming material, a message is sent to controller 62 requesting a diversion of the mailpiece to content testing laboratory 171. Process 170 is described in the descriptions of FIGS. 6 and 7. Laboratory 171 performs various tests on the mailpiece, e.g., weighing, x-raying, detecting the emission of volatile organic chemicals, detecting the emission of heat, detecting the presence of radioactivity, using sonograms, detecting odors, etc., to determine whether or not the mailpiece contains life harming materials. If it is determined that there it is likely that the mailpiece contains life harming materials, the mailpiece is sent to the proper authority disposal site 172. If security process 170 determines that the mailpiece does not contain life harming materials, process 170 will transfer the image to encode sort and store 53.

Figure 3:
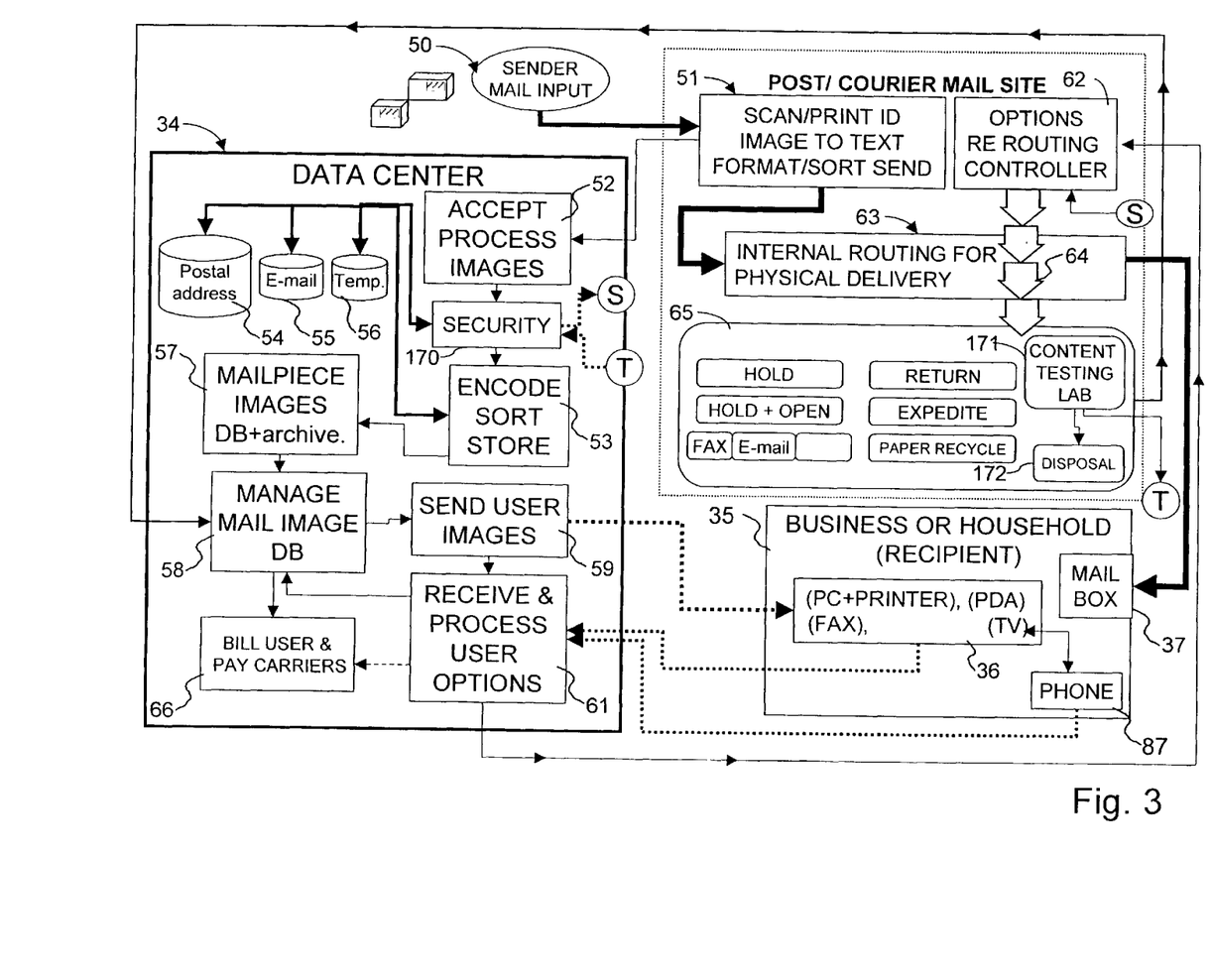
FIG. 3 is a drawing showing how this invention may be used by the post and/or a courier in the processing of flats and packages.

FIG. 3 is a drawing showing how this invention may be used by a post or courier in the processing of packages and flats. Packages and flats that are deposited with the carrier at 50 are scanned by scanner/coder 51. Scanner/coder 51 scans all of the information appearing on the face of the package or flat, e.g., (from FIG. 1D) the sender's address 41, the sender's phone number 44, the recipient's address 42 and courier symbology 43. The scanned information is coded, formatted and sorted, and the physical flat or package is sent to internal routing for physical delivery of the package or flat 63. The aforementioned information is transferred to accept process images 52, which is located at data center 34. Now the scanned information is transferred to security process 170. Process 170 transfers information to options controller 62. Process 170 will be described hereinafter in the description of FIG. 6. If process 170 decides that there is no indication that the package or flat does not contain life harming material, then the information is sent to encode, sort, store 53. At this point, the recipient's physical address is verified by checking postal address data base 54, and the recipient's e-mail address is determined from e-mail data base 55. Temporary data base 56 is then searched to determine whether or not the recipient has left any forwarding addresses. Encode 53 then encodes and sorts the information obtained from data bases 54, 55 and 56.

The aforementioned encoded and sorted information is stored in mail image archive data base 57. Then the package or flat image information is sent to manage mail image 58 where the various options and the costs associated therewith that the recipient may have for delivering the information contained in the package or flat are determined. Then the mail images and options that the recipient has for receiving the package or flat are sent to images 59, where the information appearing on the face of the package or flat in alphanumeric and graphic form and the options in alphanumeric and graphic form the recipient has for receiving the package or flat are transmitted to receiving device 36 (personal computer, television, facsimile machine, personal data assistant, etc.), which is located at the recipient's business or household 35. The recipient may use device 36 (personal computer, facsimile machine, personal data assistant, etc.) located at the recipient's business or household 35 to inform receive and process recipient options 61, located at data center 34, of the manner in which the package or flat should be delivered. The recipient may also use a touch tone and/or voice telephone 87 to inform options 61 of the manner in which the recipient would like the package or flat displayed on the receiving device 36, e.g., television delivered. For instance, the recipient may want the package or flat physically delivered to the recipients house faster or slower; or the package or flat physically redirected to the recipient's temporary address, or physically delivered to the recipient's agent; or physically delivered to the recipient's attorney; or physically returned to the mailer; or have the post open the package or flat and have the post e-mail or fax the contents of the package or flat to the recipient and/or parties designated by the recipient.

At this juncture, the recipient may inform options 61 via a device 36 of the manner in which the recipient would like the package or flat processed. Options 61 will then inform the recipient via device 36 of the cost to the recipient to deliver the package or flat in the manner selected by the recipient. The recipient may then inform the carrier to deliver the package or flat in the manner selected by the recipient. The recipient's selected manner of package or flat delivery is forwarded to options rerouting controller 62. If the carrier specified time to deliver the package or flat has not been reached or the package or flat is at internal routing for physical processing 63, the package or flat will be sent to recipient options 62 and delivered in the manner selected by the recipient in route mail options 65. Then options 65 informs manage mail data base 58 to archive the image and also to notify bill sender and pay carriers 66 to bill the recipient and pay the carrier. At this point, the next package or flat image is ready to be processed.

The package or flat may then be delivered to the recipient at mail box 37 at a faster or slower rate than that selected by the sender; held by the courier for a specified amount of time and then delivered to an address specified by the recipient; opened, and the contents of the package or flat faxed to recipient's selected fax numbers; opened, and the contents of the package or flat faxed to recipient's selected fax numbers, and then the package or flat may be delivered to the physical address specified by the recipient; opened, and the contents of the package or flat e-mailed to recipient's selected e-mail addresses; or, opened, and the contents of the package or flat e-mailed to recipient's selected e-mail addresses, and then the package or flat may be delivered to the physical address specified by the recipient. The recipient may also have instructed the post or courier to return the mail to the sender or to destroy the contents of the package or flat or recycle the contents of the package or flat. Options 61 will also send the cost of the recipient's selected manner of delivery to bill recipient 66 so that the carrier may debit the recipient's account or send a bill to the recipient.

If security process 170 determines there is an indication that the package or flat contains life harming material, a message is sent to controller 62 requesting a diversion of the package or flat to content testing laboratory 171. Process 170 is described in the descriptions of FIGS. 6 and 7. Laboratory 171 performs various tests on the package or flat, e.g., weighing, x-raying, detecting the emission of volatile organic chemicals, detecting the emission of heat, detecting the presence of radioactivity, using sonograms, detecting odors, etc., to determine whether or not the package or flat contains life harming materials. If it is determined that there it is likely that the package or flat contains life harming materials, the package or flat is sent to the proper authority disposal site 172. If security process 170 determines that the mailpiece does not contain life harming materials, process 170 will transfer the image to encode sort and store 53.

Figure 4:
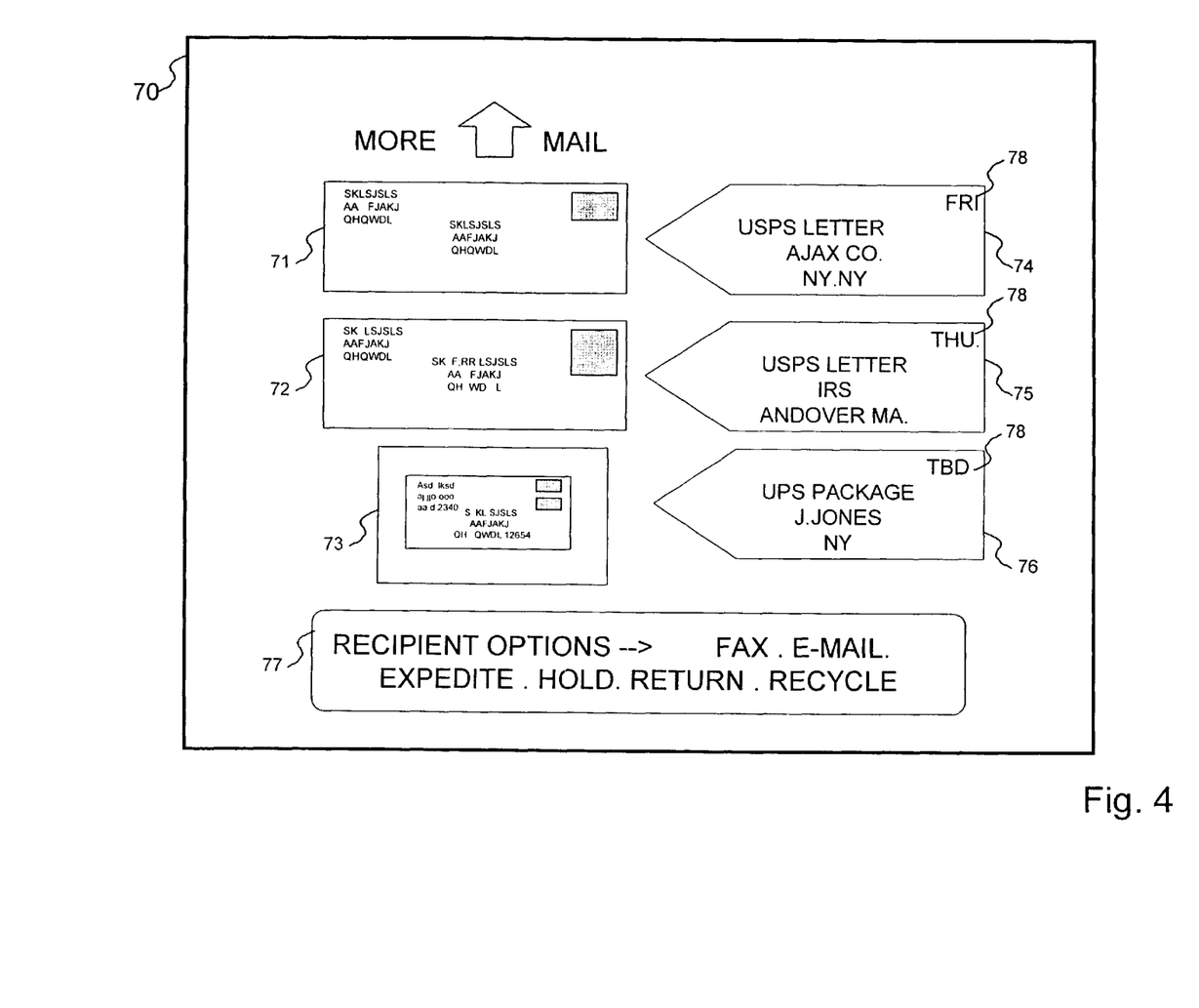
FIG. 4 is a drawing of the information that appears on one or more of receiving devices 36.

FIG. 4 is a drawing of the information that appears on one or more of receiving devices 36. The information may appear on the display of a personal computer, the screen of a television set, or paper 70 printed by a printer or facsimile machine. An image of the face of a letter mailpiece is shown at 71 and 72, and an image of the face of a flat or package is shown at 73. Data associated with letter mailpiece 71 is shown at 74, and data associated with letter mailpiece 72 is shown at 75. Data associated with package or flat 73 is shown at 76. The options that the recipient has for diverting the mail are shown at 77, and the estimated time of arrival of delivery is shown at 78.

Figure 5:
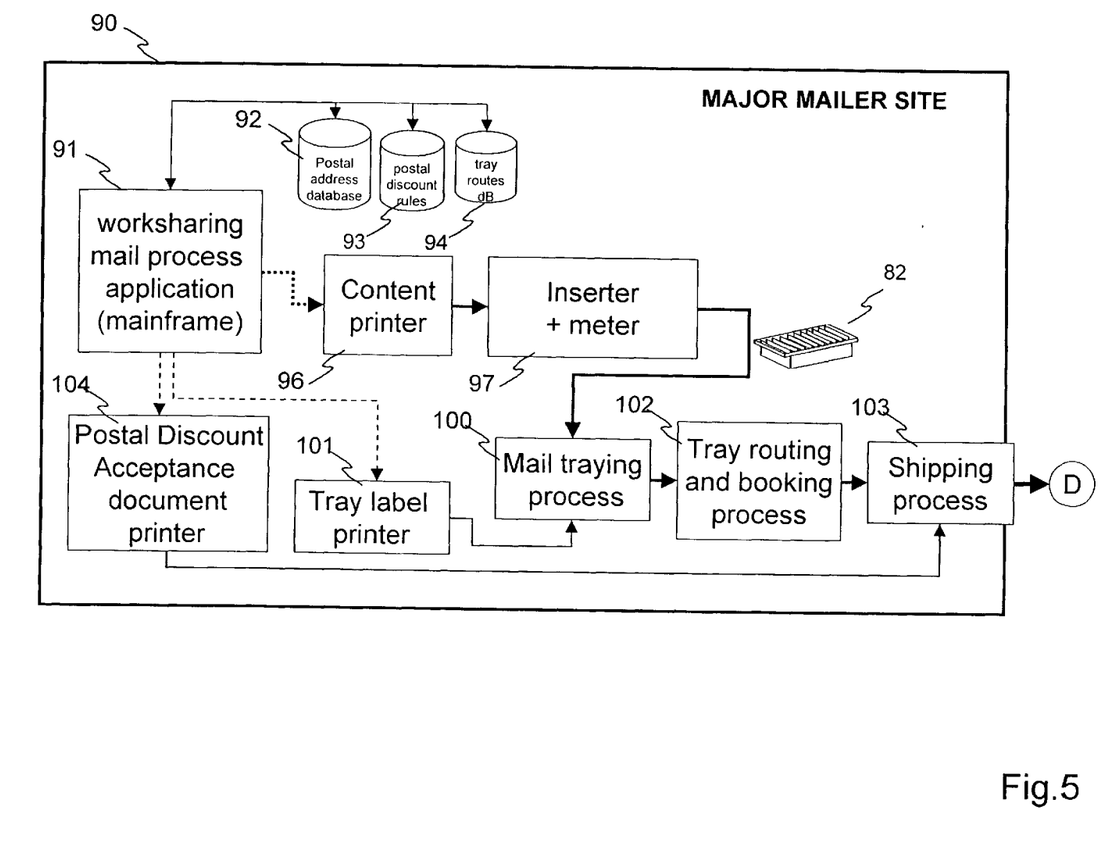
FIG. 5 is a drawing of major mailer site 90.

FIG. 5 is a drawing of major mailer site 90 that is used in the production of mailpieces for trays 82 (shown in FIG. 2). A mainframe computer 91 is located at site 90. Computer 91 performs preprocessing of the letter mailpiece by controlling the content and composition of the letter mailpiece as well as the address management, presortation postal requirements and postal process bar code requirements. Computer 91 is coupled to postal address data base 92, postal discount rules 93, and tray routes database 94. Computer 91 utilizes data base 92, rules 93 and data base 94 to instruct content printer 96 to print the material that is required for the mailing, e.g., information appearing on the face of the letter mailpiece; and material that is going to be inserted into the mailpiece. Inserter and meter 97 inserts the material into the correct mailpiece, seals the mailpiece, applies the correct postage to the mailpiece, places the mailpiece in the proper tray 82, and prepares documentation for the mailpieces in tray 82. Computer 91 will cause tray label printer 101 to print a label according to mail traying process 100 for the tray 82 that inserter and meter 97 is filling. Then the trays 82 containing the letter mailpieces go to tray routing and booking process 102 and shipping process 103. When the trays 82 are in shipping process 103, postal discount acceptance printer 104 will be instructed by computer 91 to print the proper postal documentation for the letter mailpieces in tray 82. After process 93 places the proper documentation in trays 82, trays 82 are ready to be shipped to delivery bar code sorter/code printer 25 or sequence bar code sorter/code printer 26 (FIG. 2).

Figure 6:
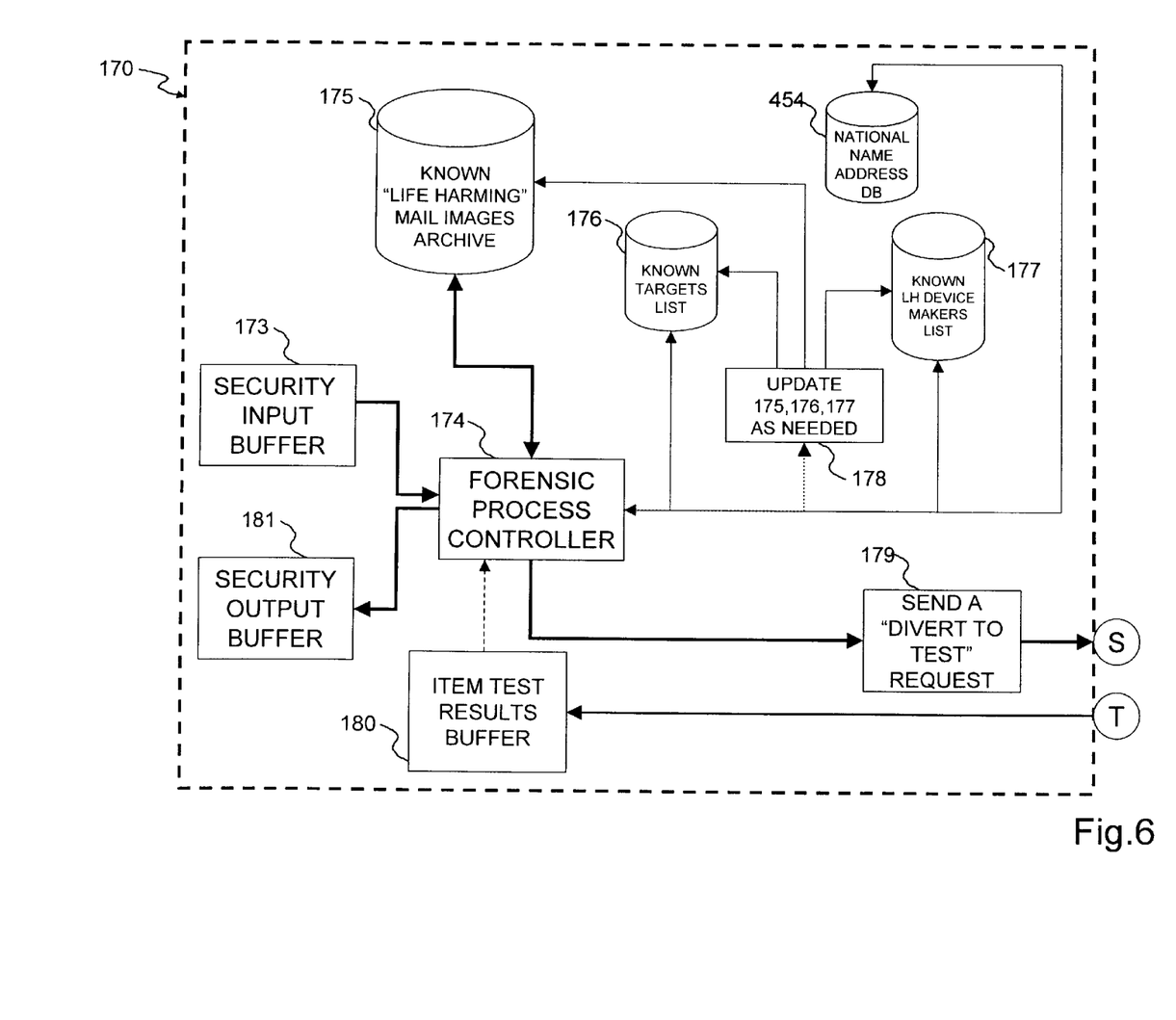
FIG. 6 is a drawing of the security process for the mailpiece.

FIG. 6 is a drawing of the security process 170 for the mail. Security input buffer 173 receives the output of accept images 52 (FIG. 2 or FIG. 3). The output of images 52 will be a data base record file that is similar to the mailpiece data base record file described in FIG. 8. The data base record file is sent to forensic process controller 174. A flow chart describing the operation of controller 174 is described in FIG. 7. Controller 174 is coupled to life harming mail images archive 175. Archive 175 maintains images of the faces of mail that proved to be suspicious in the past. Controller 174 will check if the image of the mail presently being reviewed is similar to an image in archive 175, e.g., it contains a similar graphic, the wrapping paper is the same, etc. Controller 174 is coupled to national name and address data base 454; targets list 176; manufacturers of life harming materials and people who are likely to distribute life harming materials list 177; update mail file archive 178; send divert to test request 179; items test results buffer 180; and security output buffer 181. Data base 454 maintains a national list of the name and postal address of every known person living in the United States and targets list 176 includes government leaders, industrial leaders, noted personalities, people to whom threats have been made and people who want to be included on the list, etc. List 177 includes manufacturers of life harming materials and people who are likely to distribute life harming materials legally or illegally, and update mail file archive 178 controls the updating of lists 176 and 177. Send a divert to test request 179 sends the mail to controller 62 in FIG. 2 for letter mailpieces and to controller 62 in FIG. 3 for a package or flat, and then the mail is sent to content testing laboratory 171 to check for life harming materials. Item test results buffer 180 receives the results from testing laboratory 171 and sends the results to controller 174. Controller 174 updates data bases 175, 176 and 177. If laboratory 171 determines that there is no life harming material in the mail, security output buffer 181 receives an image from controller 174 and sends the image to encode sort store 53 (FIG. 2) for a letter mailpiece and sort store 53 (FIG. 3) for a package or flat. If laboratory 171 determines that there is life harming material in the mail, security output buffer 181 receives an image from controller 174 and sends the image to encode sort store 53 (FIG. 2) for a letter mailpiece and sort store 53 (FIG. 3) for a package or flat. The letter mailpiece, package, or flat will then be destroyed by disposal 172.

Figure 7:
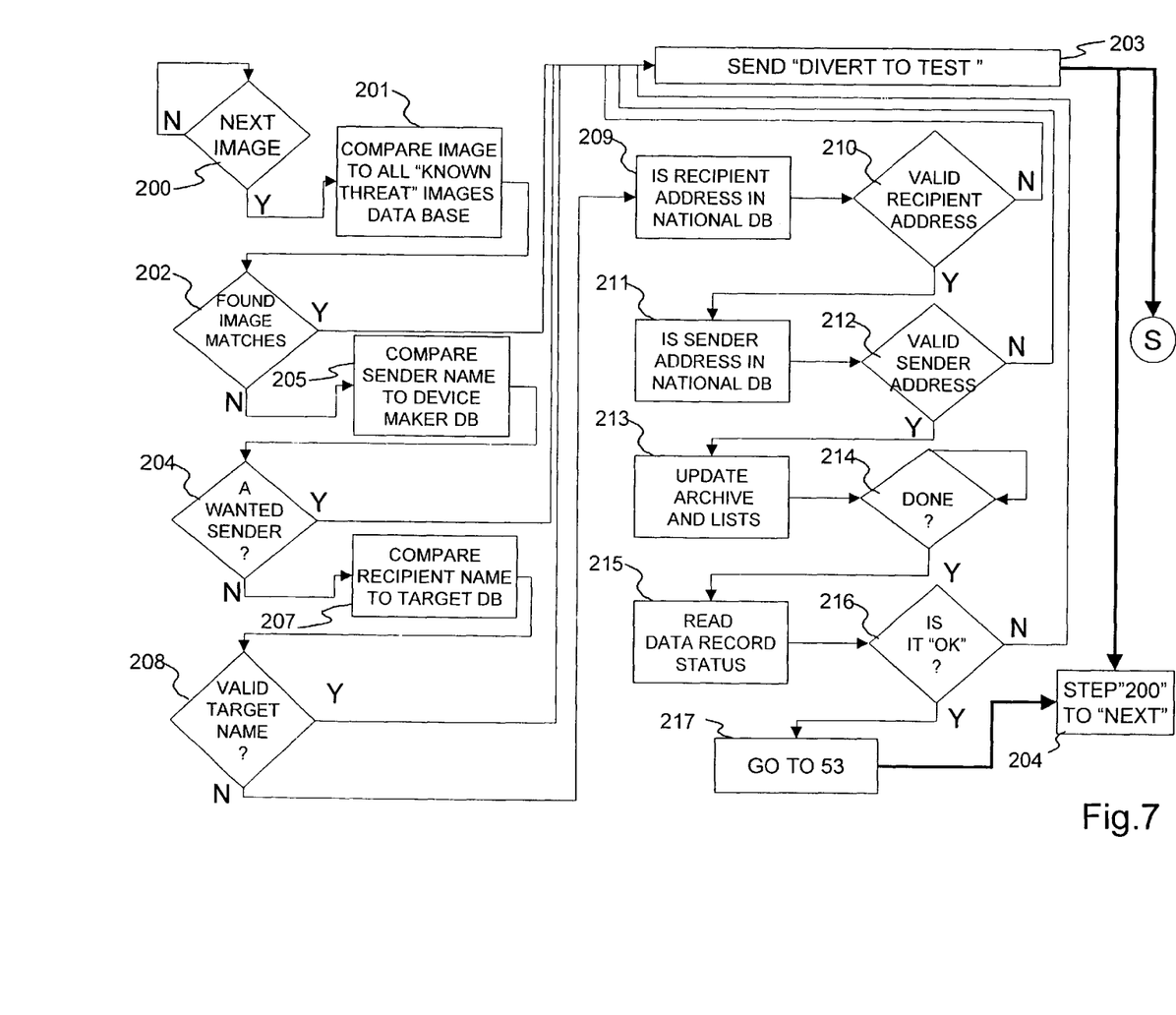
FIG. 7 is a flow chart that describes the operation of controller 174 of FIG. 6.

FIG. 7 is a flow chart that describes the operation of controller 174 of FIG. 6. The program begins in decision block 200. Block 200 determines whether or not the next mail image is present. If block 200 determines that the next mail image is not present, the program goes back to the input of block 200. If block 200 determines that the next mail image is present, the program goes to block 201 to check life harming image data base 175 (FIG. 6) to see if the mail face image contains known visual threat indicators. Some known visual threat indicators are no return address found; the return address for the city or zip code does not match the cancellation city or zip code of the cancelled mail; restrictive markings on mail; e.g., private, to be opened by addressee only, etc.; the data in the postal indicia indicates that the indicia has been previously used; the date in the postal indicia indicates that the mail is old; the postal indicia does not contain a valid meter account number; the permit indicia has been previously used; the font or handwriting used on the face of the mail matches fonts or handwriting previously used on mail containing life harming materials used by illegal sources; the misspellings on the face of the mail match misspellings previously used on mail containing life harming materials used by illegal sources; the texture on the mail and/or watermarks on the mail or other items on the mail match the texture on the mail and/or watermarks on the mail or other items on the mail previously used on mail containing life harming materials used by illegal sources; the graphics on the mail match previously used graphics on mail containing life harming materials used by illegal sources; the label stock, size, color shape or texture matches previously used label stock, size, color, or texture on mail containing life harming materials used by illegal sources; the meter tape used, type, size, shape, watermark, etc., matches previously used meter tapes on mail containing life harming materials used by illegal sources; or some characteristic of the tape used to seal or wrap the mail matches a tape used on mail containing life harming materials used by illegal sources.

Now decision block 202 will determine whether or not two items in the mail image match two threat indicators stored in data base 175. If block 202 determines that there are two items in the mail image that match two threat indicators stored in data base 175, the program goes to block 203 to request that the mail be diverted by controller 62 to content testing laboratory 171. Laboratory 171 will determine whether or not the mail contains life harming materials. Then the program goes to block 204 and then back to the input of block 200. If block 202 determines that there are two items in the mail image that match two threat indicators stored in data base 175, the program goes to block 203 to request that the mail be diverted by controller 62 to content testing laboratory 171. If block 202 determines that there are not two items in the mail image that match two threat indicators stored in data base 175, the program goes to block 205. Block 205 reads the sender's name and the information in data base 177. Then the program goes to decision block 204. Block 204 determines whether or not the sender's name matches the information in data base 177. If block 204 determines that the sender's name matches the information in block 177, the program goes to block 203 to request that the mail be diverted by controller 62 to content testing laboratory 171. If block 204 determines that the sender's name does not match the information in block 177, the program goes to block 207. Block 207 reads the recipient's name and the information in target list 176. Then the program goes to the input of decision block 208. Block 208 determines whether or not the recipient's name matches the information in data base 176. If block 208 determines that the recipient's name matches the information in block 176, the program goes to block 203 to request the mail be diverted by controller 62 to content testing laboratory 171. If block 208 determines that the recipient's name does not match the information in block 176, the program goes to block 209. Block 209 reads the recipient's address and the address information in national name and address data base 454. Then the program goes to the input of decision block 210. Block 210 determines whether or not the recipient's address matches the address information in data base 454. If block 210 determines that the recipient's address matches the information in block 209, the program goes to block 203 to request the mail be diverted by controller 62 to content testing laboratory 171. If block 210 determines that the recipient's name does not match the information in block 209, the program goes to block 211. Block 211 reads the sender's address and the address information in national name and address data base 454. Then the program goes to the input of decision block 212. Block 212 determines whether or not the sender's address matches the address information in data base 454. If block 212 determines that the sender's address does not match the information in block 211, the program goes to block 203 to request the mail be diverted by controller 62 to content testing laboratory 171. If block 212 determines that the sender's address matches the information in block 211, the program goes to block 213.

Block 213 updates lists 176 and 177. Then the program goes to the input of decision block 214. Block 214 determines whether or not lists 176 and 177 have been updated. If block 214 determines that lists 176 and 177 have not been updated, the program goes back to the input of block 214. If block 214 determines that lists 176 and 177 have been updated, the program goes to block 215. Block 215 reads data status record 228 (FIG. 9). Then the program goes to the input of decision block 216. Block 216 determines whether or not data status record 228 is correct. If block 216 determines that record 228 is not correct, the program goes to block 203 to request the mail be diverted by controller 62 to content testing laboratory 171. If block 216 determines that record 228 is correct, the program goes to block 217. Block 217 sends the program to block 53 encode, sort, store (FIGS. 2 and 3) and to block 204, which steps the program back to the input of block 200.

Figure 8:
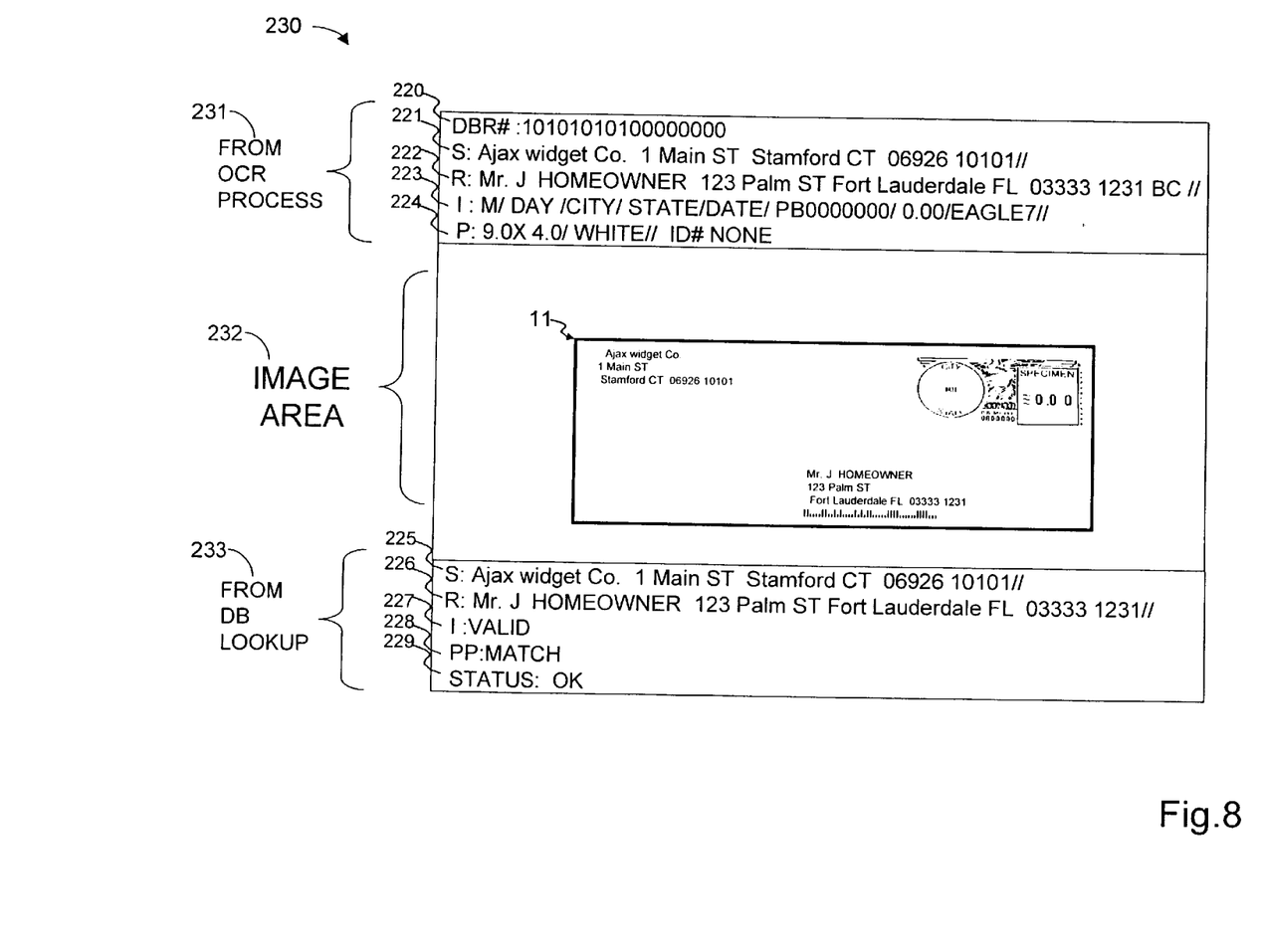
FIG. 8 is a drawing of a record file for a typical mailpiece.

FIG. 8 is a drawing of a record file 230 for a typical mailpiece. File 230 includes an area 231 that represents matter obtained from scanning the mail; an image area 232 that shows an image of the face of the mail, e.g., mailpiece 11, and area 233 that represents information obtained from processing the scanned image of mailpiece 11. Area 231 includes item 220 that represents the data base record number for this file; item 221 that represents the name and address of the sender of letter mailpiece 11; item 222 that represents the name and address of the recipient of mailpiece 11; item 223 that represents information contained in the postal indicia of mailpiece 11; and item 224 that represents information regarding the physical characteristics of the envelope used for mailpiece 11.

Area 233 includes item 225 represents the name and address of the sender of letter mailpiece 11 that has been obtained from data base 454 (FIGS. 2 and 3). Item 226 represents the name and address of the recipient of letter mailpiece 11 that has been obtained from data base 454 (FIGS. 2 and 3). Item 227 indicates that the indicia is valid. Item 228 indicates whether or not there was a match between the image of mailpiece 11 and an image of mailpiece 11 stored in archive 175. Item 229 indicates the status of file 230.

The above specification describes a new and improved method that enables a carrier to determine whether or not mail contains life harming materials. It is realized that the above description may indicate to those skilled in the art additional ways in which the principles of this invention may be used without departing from the spirit. Therefore, it is intended that this invention be limited only by the scope of the appended claims.

What is claimed is:

1. A method for a carrier to determine whether or not mail contains life harming materials, said method comprises the steps of:

receiving mail that is addressed to a recipient which contains material that may or may not be life harming;

capturing an image of the face of the mail, which includes the name and physical address of the recipient;

determining whether the carrier has been notified that mail addressed to particular recipients should be checked to see if it contains life harming material;

processing the image on the face of the mail to determine if characteristics of the image match characteristics of known mail that may contain life harming materials;

testing the mail if the image contains characteristics of life harming material; and delivering the mail to the recipient if the image does not contain life harming characteristics.

2. The method claimed in claim 1, further including the steps of:

capturing an image of the face of the mail, which includes the name and physical address of sender and;

determining whether the carrier has been notified that mail sent by particular senders should be checked to see if it contains life harming material.

3. The method claimed in claim 1, further including the step of placing a unique number on the mail to positively identify the mail.

4. The method claimed in claim 1, wherein the testing step further includes the step of weighing the mail.

5. The method claimed in claim 1, wherein the testing step further includes the steps of x-raying the mail.

6. The method claimed in claim 1, wherein the testing step further includes the step of detecting the emission of volatile organic chemicals from the mail.

7. The method claimed in claim 1, further including the step of charging the recipient for determining whether or not recipient mail is likely to contain life harming materials.

8. The method claimed in claim 1, further including the step of charging the recipient for disposing of mail that is likely to contain life harming materials.

* * * * *